(12) United States Patent
Rohl et al.

(10) Patent No.: US 10,231,717 B2
(45) Date of Patent: Mar. 19, 2019

(54) BIOPSY NEEDLE

(71) Applicant: BOSTON SCIENTIFIC SCIMED, INC., Maple Grove, MN (US)

(72) Inventors: James P. Rohl, Prescott, WI (US); Katharine Eckerline, Boston, MA (US); Michael J. Rebrovich, Lino Lakes, MN (US); David Lehse, Oakdale, MN (US); Christopher A. Benning, Hopkinton, MA (US); Oscar R. Carrillo, Jr., Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 284 days.

(21) Appl. No.: 15/172,533

(22) Filed: Jun. 3, 2016

(65) Prior Publication Data

US 2016/0354067 A1    Dec. 8, 2016

Related U.S. Application Data

(60) Provisional application No. 62/171,404, filed on Jun. 5, 2015.

(51) Int. Cl.
*A61B 5/00* (2006.01)
*A61B 10/02* (2006.01)
*A61B 10/04* (2006.01)

(52) U.S. Cl.
CPC .......... *A61B 10/0283* (2013.01); *A61B 10/04* (2013.01); *A61B 10/0275* (2013.01); *A61B 2010/045* (2013.01)

(58) Field of Classification Search
CPC . A61B 10/02; A61B 10/0233; A61B 10/0275; A61B 10/0283; A61B 10/04; A61B 2010/045
USPC .......................................................... 600/570
See application file for complete search history.

(56) References Cited

U.S. PATENT DOCUMENTS

| | | | | |
|---|---|---|---|---|
| 5,048,530 A | * | 9/1991 | Hurwitz | A61B 8/0833 600/461 |
| 5,199,441 A | * | 4/1993 | Hogle | A61B 10/0283 600/566 |
| 5,807,282 A | * | 9/1998 | Fowler | A61B 10/0291 600/571 |
| 5,843,111 A | | 12/1998 | Vijfvinkel | |
| 6,086,543 A | | 7/2000 | Anderson et al. | |
| 8,858,461 B2 | * | 10/2014 | Persat | A61B 10/0275 600/562 |
| 2003/0114773 A1 | | 7/2003 | Janssens | |

(Continued)

FOREIGN PATENT DOCUMENTS

GB    2 255 282    11/1992
WO    2012/0106293    8/2012

*Primary Examiner* — Max Hindenburg
(74) *Attorney, Agent, or Firm* — Fay Kaplun & Marcin, LLP

(57) ABSTRACT

A device for collecting a tissue sample includes a needle body extending along a longitudinal axis from a proximal end to a distal end and including a channel extending longitudinally therethrough and a plurality of cut outs extending laterally into the needle body, each of the plurality of cut outs extending at an angle relative to the longitudinal axis from an outer surface of the needle body toward the distal end thereof so that the channel is open to an exterior of the needle body via the plurality of cut outs.

9 Claims, 4 Drawing Sheets

(56) References Cited

U.S. PATENT DOCUMENTS

2012/0197157 A1  8/2012  Ryan et al.
2013/0123623 A1  5/2013  Nishina et al.

* cited by examiner

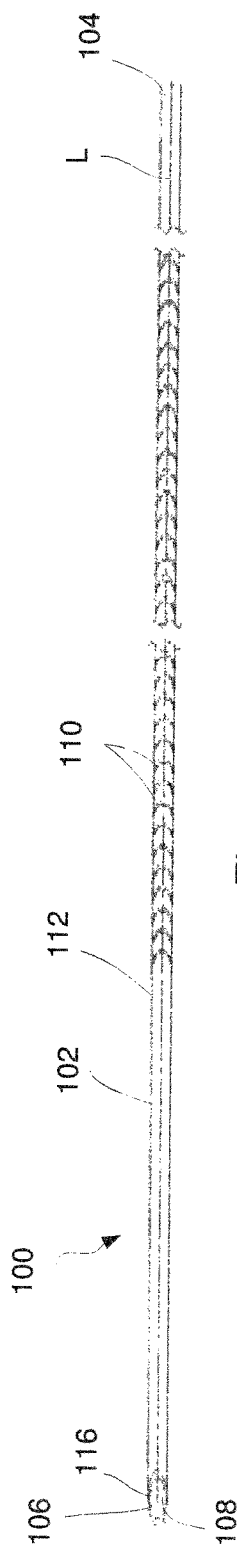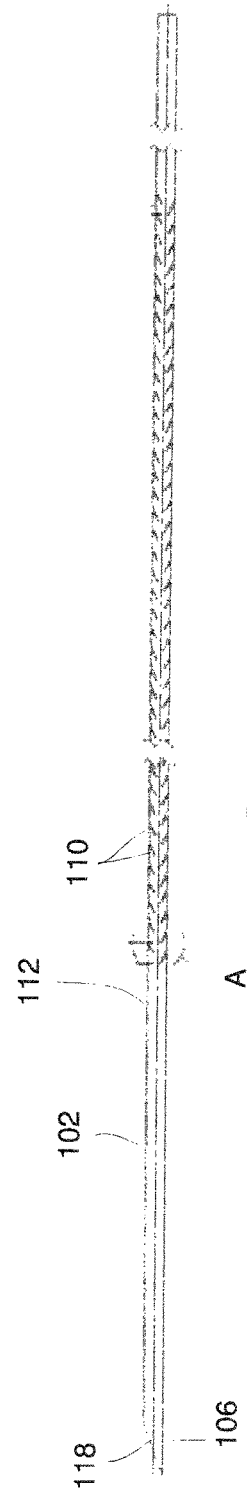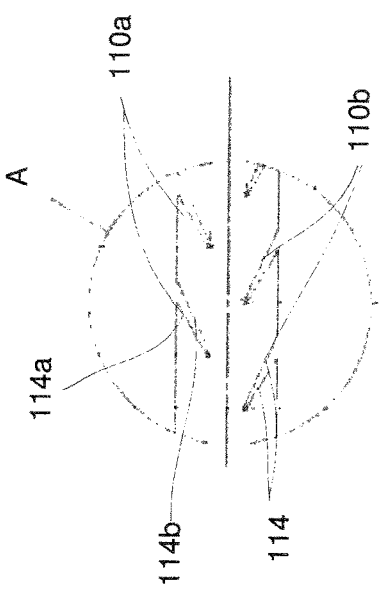

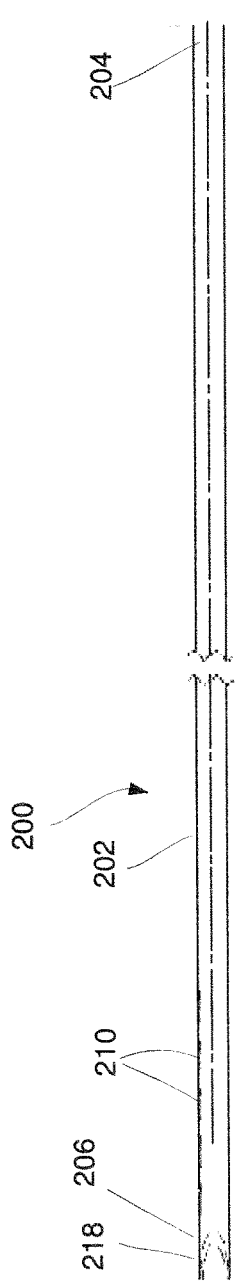
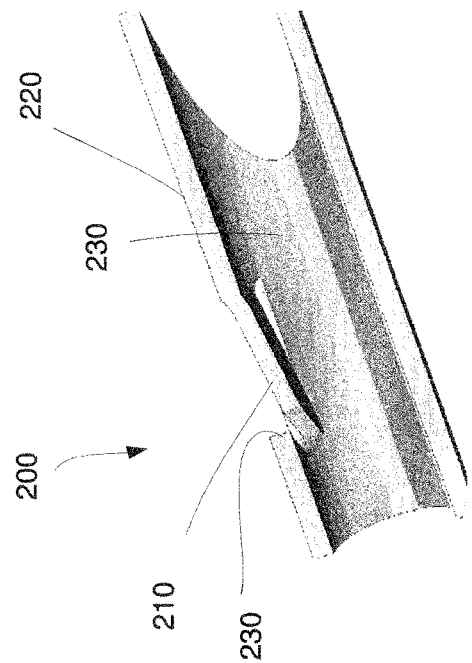
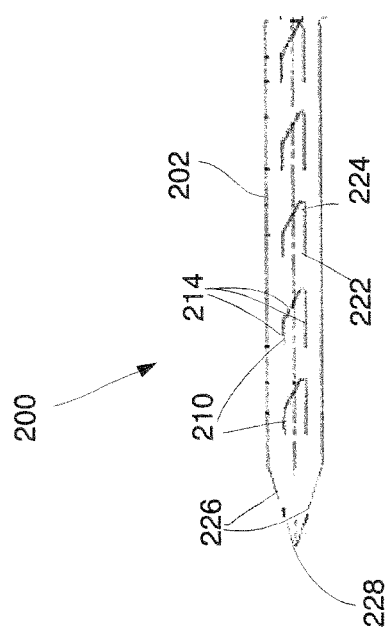

BIOPSY NEEDLE

PRIORITY CLAIM

This application claims priority to U.S. Provisional Patent Application Ser. No. 62/171,404 filed Jun. 5, 2015; the disclosure of which is incorporated herewith by reference.

BACKGROUND

Needle biopsy procedures are common for the diagnosis and the staging of disease. For example, a fine needle aspiration needle may be advanced through a working channel of an endoscope to a target tissue site. Although fine needle aspiration is a highly sensitive and specific procedure, it is often difficult to acquire a suitable sample under certain clinical situations. The more cells or tissue that can be acquired, the greater the potential for a definitive diagnosis. Larger gauge needles, however, are difficult to pass along tortuous paths through the anatomy to target sites and may acquire samples including more blood, making it more difficult to obtain a diagnosis.

SUMMARY

The present disclosure relates to a device for collecting a tissue sample, comprising a needle body extending along a longitudinal axis from a proximal end to a distal end and including a channel extending longitudinally therethrough and a plurality of cut outs extending laterally into the needle body, each of the plurality of cut outs extending at an angle relative to the longitudinal axis from an outer surface of the needle body toward the distal end thereof so that the channel is open to an exterior of the needle body via the plurality of cut outs.

In an embodiment, a first set of the plurality of cut outs may extend along a length of a first side of the needle body.

In an embodiment, a second set of the plurality of cut outs may extend along a length of a second side of the needle body substantially opposing the first side.

In an embodiment, a portion of a wall between adjacent cut outs may be crimped inward toward a longitudinal axis of the needle body so that the portion of the wall extends into the channel.

In an embodiment, each of the plurality of cut outs may be equally spaced from one another along a length of the needle.

In an embodiment, each of the plurality of cut outs may be defined via a first edge and a second edge which meet at an acute angle.

In an embodiment, each of the plurality of cut outs may extend at an angle relative to the longitudinal axis ranging from between 0 and 90 degrees.

In an embodiment, edges of the plurality of cut outs may be sharpened to cut tissue as the device is being withdrawn from a target tissue.

In an embodiment, the plurality of cut outs may be formed via one of laser cutting, electric discharge machining and stamping.

In an embodiment, the distal end of the needle body may include a tapered distal tip.

The present disclosure also relates to a device for collecting a tissue sample, comprising a needle body extending along a longitudinal axis from a proximal end to a distal end and including a channel extending longitudinally therethrough and a plurality tabs formed in a wall of the needle body, the tabs defined via cuts extending through the wall such that each tab extends from a distal end connected to the wall to a free proximal end so that the channel is open to an exterior of the needle body via the cuts.

In an embodiment, the distal end of the needle body may include a tapered tip.

In an embodiment, the tapered tip may include a pointed tip within a plane extending through the longitudinal axis of the needle body.

In an embodiment, at least one of the plurality of tabs may be crimped inward toward the longitudinal axis of the needle body so that the proximal end of the at least one tab extends into the channel.

In an embodiment, a proximal edge of an opening formed in the wall via the at least one crimped tab may be configured to cut tissue as the needle body is inserted distally into target tissue.

The present disclosure also relates to a method for collecting a tissue sample comprising inserting a needle to a target tissue within a living body via a working channel of an endoscope, moving the needle distally into the target tissue so that a distal end of the needle is inserted into the target tissue and a tissue sample is collected within a channel thereof, and retracting the needle proximally from the target tissue so that cut outs extending laterally into the needle at an angle relative to a longitudinal axis thereof cut a surrounding tissue and receive additional tissue therethrough into the channel.

BRIEF DESCRIPTION

FIG. 1 shows a longitudinal side view of a device according to an exemplary embodiment of the present disclosure;

FIG. 2 shows another longitudinal side view of the device of FIG. 1; and FIG. 3 shows an enlarged view of a portion A of the device of FIG. 2;

FIG. 9 shows another longitudinal side view of the device of FIG. 8;

FIG. 10 shows an enlarged longitudinal side view of a distal portion of the device of FIG. 8; and FIG. 11 shows an enlarged longitudinal cross-sectional view of a portion of the device of FIG. 8.

DETAILED DESCRIPTION

Figure 4:
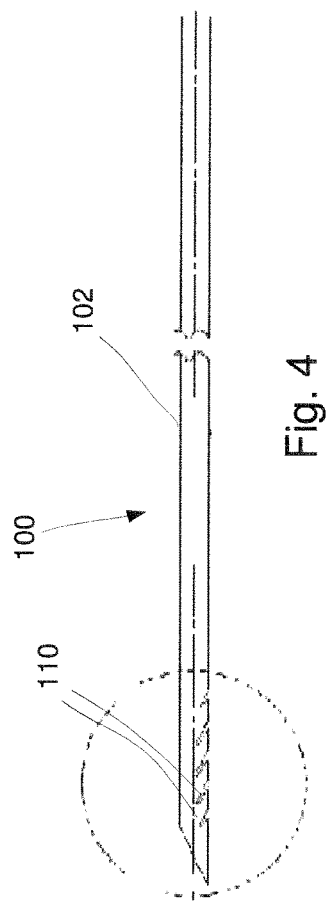
FIG. 4 shows a longitudinal side view of a device according to yet another exemplary embodiment shows a longitudinal side view of a distal portion of a device, according to another exemplary embodiment.

The present disclosure may be further understood with reference to the following description and the appended drawings, wherein like elements are referred to with the same reference numerals. The present disclosure relates to biopsy devices and, in particular, relates to needles for collecting a tissue sample. Exemplary embodiments of the present disclosure describe a needle including angled cut outs extending therealong to form cutting edges which facilitate the collection of additional tissue as the needle is being drawn proximally out of a tissue sample. It should be noted that the terms "proximal" and "distal" as used herein are intended to refer to a direction toward (proximal) and away from (distal) a user of the device.

As shown in FIGS. 1-3, a needle device 100 according to an exemplary embodiment of the present disclosure comprises a needle body 102 defining a channel 108 extending longitudinally therethrough and a plurality of cut outs 110 extending laterally into the needle body 102 such that the channel 108 is open to an exterior of the needle body 102 via the cut outs 110. The cut outs 110 in this embodiment extend into the needle body 102 angled relative to a longitudinal axis L of the needle body 102 (e.g., cut outs 110 may extend from more than 0 degrees relative to the longitudinal axis L up to 90 degrees) such that, when the needle device 100 is inserted distally into target tissue to collect a tissue sample in the channel 108, liquids and gases are vented out of the channel 108 via the cut outs 110. As the needle device 100 is retracted proximally from the target tissue, edges 114 of the cut outs 110 cut a surrounding portion of the target tissue to collect additional tissue which is lodged in the channel 108 via the cut outs 110. Thus, the needle device 100 is able to collect a larger tissue sample in the channel 108 than is a standard needle lacking such cut outs.

The needle body 102 extends along the longitudinal axis L from a proximal end 104 to a distal end 106. The channel 108 extends longitudinally through the needle body 102 to a distal opening 116 through which a portion of the target tissue may be received in the channel 108. The distal end 106 of this embodiment includes a tapered tissue-piercing tip 118. As would be understood by those skilled in the art, the needle body 102 of this embodiment is formed of a material having flexibility sufficient to permit the needle body 102 to be inserted through the tortuous paths of a body lumen—i.e., a flexibility sufficient to enable the needle body 102 to be inserted to the target tissue along a curved path traversed via, for example, a flexible endoscope. The needle body 102 according to this embodiment is preferably sized and shaped for insertion through the working channel of a flexible endoscope. However, as would be understood by those skilled in the art, the size and shape of the needle body 102 may be altered to facilitate its insertion via any other suitable insertion device. For example, the needle body 102 may range from between 18 gauge to 27 gauge. A size of the needle body 102 may be selected to achieve a desired result and/or to be inserted through any number of insertion devices. The needle body 102 may be formed of any of a variety of materials such as, for example, Nitinol, stainless steel, cobalt-chromium, polymers and/or any combination thereof.

In one exemplary embodiment, a first set of cut outs 110a extends along a length of a first side of the needle body 102 with the first set of cut outs 110a substantially parallel to one another aligned along the length thereof. The needle body 102 according to this embodiment further includes a second set of cut outs 110b extending along a second side of the needle body 102 substantially opposite the first side with the second set of cut outs 110b substantially parallel to one another. In this embodiment, each of the first cut outs 110a is formed as a slice extending distally into the needle body 102 from an open end toward closed ends on a first side of the needle body 102 while each of the second cut outs 110b is formed as a slice extending distally into the needle body 102 toward a separation between the first and second sides of the needle body 102—e.g., a plane extending through the longitudinal axis L of the needle body 102. In this embodiment, each of the first and second cut outs 110a, 110b, respectively, extends away from the plane separating the first and second sides of the needle body 102 at an acute angle with the angle formed by each first cut out 110a being substantially equal to and opposite the angle formed by each of the second cut outs 110b. As, in this embodiment, the first cut outs 110a are longitudinally offset from the second cut outs 110b, the closed ends of each first cut out 110a are located longitudinally between the closed ends of an adjacent pair of second cut outs 110b. In an exemplary embodiment, the cut outs 110 are equally spaced from one another along the length of the needle body 102. Although the exemplary embodiment shows and describes a first and second set of cut outs 110a, 110b, the needle body 102 may alternatively include cut outs 110 only along one side of the needle body 102.

Each of the cut outs 110 may be formed by, for example, one of laser cutting, electrical discharge machining, or stamping. Each of the cut outs 110 may be formed by a pair of cuts extending laterally into the needle body 102 at an angle relative to the longitudinal axis L so that each cut out 110 is defined by two edges 114a, 114b which meet at an acute angle relative to one another. The edges 114a, 114b extend laterally from an outer surface 112 of the needle body 102 toward the distal end 106 as the edges 114a, 114b approach the longitudinal axis L. Each of the edges 114, 114b may extend at an angle ranging from between 0 and 90 degrees relative to the longitudinal axis L of the needle body 102. More particularly, each of the edges 114a, 114b may extend at an angle between 20 and 60 degrees relative to the longitudinal axis L. The two edges 114a, 114b according to this embodiment are separated from one another by a small distance along the outer surface 112 so that the cut out 110 defines a small opening through which tissue may be received into the channel 108. In one example, the first edge 114a may extend at an angle of 30 degrees relative to the longitudinal axis L while the second edge 114b may extend at an angle of 25 degrees relative to the longitudinal axis L such that there is an angle of 5 degrees between the two edges 114a, 114b. The angle between the edges 114a, 114b, however, may vary so long as each of the edges 114a, 114b fall within the acceptable range of angles relative to the longitudinal axis L. In one embodiment, the angle between the first and second edges 114a, 114b may range from between 3 and 15 degrees. The edges 114a, 114b may also be sharpened so that they cut surrounding tissue to sever a tissue sample from the surrounding tissue as the needle device 100 is drawn proximally out of the target tissue. As described above, the angle of the cut outs 110 permits the cut outs 110 to vent liquids and/or gases therethrough as the needle device 100 is moved distally into the target tissue and to cut and collect tissue as the needle device 100 is withdrawn from the target tissue. The angles of each of the cut outs 110 may be selected to achieve the desired effect described above. The angles may vary depending on a size of the channel 108 and/or a wall thickness of the needle body 102.

Figure 5:
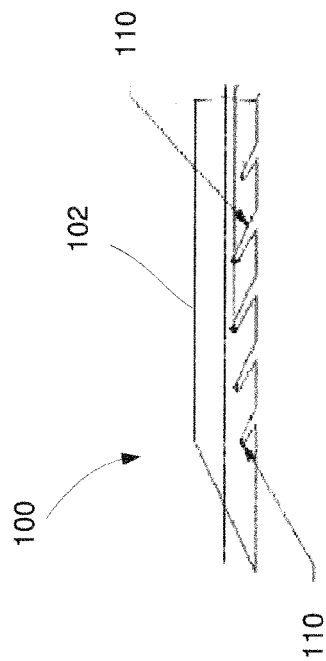
FIG. 5 shows an enlarged longitudinal side view of a distal portion of the device of FIG. 4.
Figure 6:
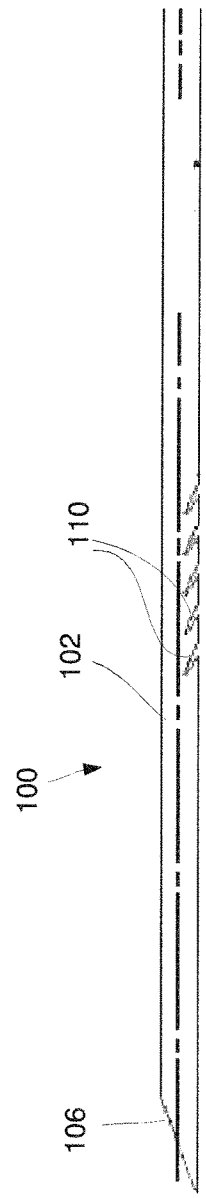
FIG. 6 shows a longitudinal side view of a device according to an alternate embodiment.

The number, density and/or characteristics of cut outs 110 may be varied along the needle body 102 depending on a target tissue consistency and bend flex requirements of the device 100. For example, a depth and area of the cut out 110 may be selected to adjust a bend strength of the needle body 102. As shown in FIG. 5, each of the cut outs 110 may vary in depth and/or area along a length of the needle body 102. The cut outs 110 may extend along a distal portion of the needle body 102, as shown in FIG. 4, and/or further proximally along the needle body 102—i.e., distanced from the distal 106, as shown in FIG. 6. Alternatively, groups of cut outs 110 may extend along select portions of a length of the needle body 102. In one embodiment, adjacent cut outs 110 may be equidistant from one another. In another embodiment, a distance between adjacent cut outs 110 may vary along the length of the needle body 102.

Figure 7:
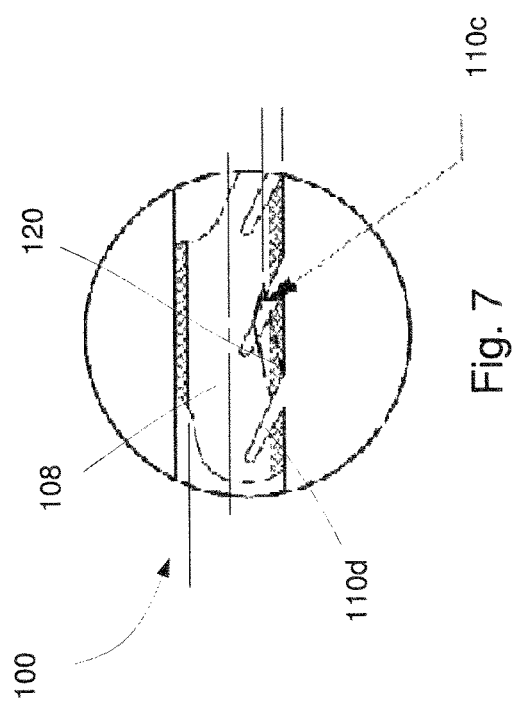
FIG. 7 shows an enlarged, longitudinal cross-sectional view of a portion of a device according to a further exemplary embodiment.

According to a further embodiment, as shown in FIG. 7, a portion of a wall 120 of the needle body 102 between adjacent cut outs 110c, 110d may be crimped to enhance a strength of a hold of the tissue sample within the channel 108. In other words, the portion of the wall 120 of the needle body 102 between adjacent cut outs 110 may be pushed inward toward the longitudinal axis L. In particular, the portion of the wall 120 proximate a proximal one 110c of the two adjacent cut outs 110c, 110d may be crimped inward, as shown in broken lines in the FIG. 7. Thus, the device 100 may still be inserted distally into the target tissue without catching on the target tissue during insertion. The crimped portion of the wall 120 provides additional internal surface area for the tissue to interface with, thereby increasing the surface tension and adding needle holding force to keep the collected tissue sample within the channel 108. Portions of the wall 120 may be crimped, as desired. All portions of wall between all of the adjacent cut outs 110 are not required to be crimped.

According to another embodiment, the cut outs 110 may be covered and/or filled with a porous material such as, for example, etched metals, ceramics or porous membranes (e.g., PTFE, PVDF-HFP) that allow fluid to transfer therethrough, but which keep the cut outs 110 from catching or collecting tissue externally. Thus, in this embodiment, the tissue sample collected within the channel 108 may be vented, but the cut outs 110 will not collect any tissue as the device 100 is being withdrawn proximally from the tissue.

According to an exemplary method for collecting a tissue sample using the needle device 100, the needle body 102 is inserted to the site of target tissue via, for example, a working channel of an endoscope. The distal end 106 of the needle body 102 is inserted distally into the target tissue so that the a portion of the target tissue is received in the channel 108 through the distal opening 116. As tissue is being collected in the channel 108 via the distal motion of the needle device 100, liquids and/or gases in the channel 108 are vented out of the channel 108 via the cut outs 110. Once a desired tissue sample has been collected within the channel 108, the needle body 102 is withdrawn proximally from the target tissue, and, as the needle device 100 is withdrawn from the target tissue, edges 114 of the cut outs 110 cut additional sample tissue from the surrounding tissue which enters the channel 108 via the cut outs 110.

In a further embodiment, a vacuum source may be connected to the proximal end 104 of the needle body 102 to apply a suction force through the channel 108 to aid in the collection of tissue as the needle device 100 is being inserted into the target tissue. Sample tissue collected within the channel 108 may later (i.e., after the needle device 100 has been withdrawn from the body) be flushed out of the channel 108 for collection using, for example, a saline solution.

Figure 8:
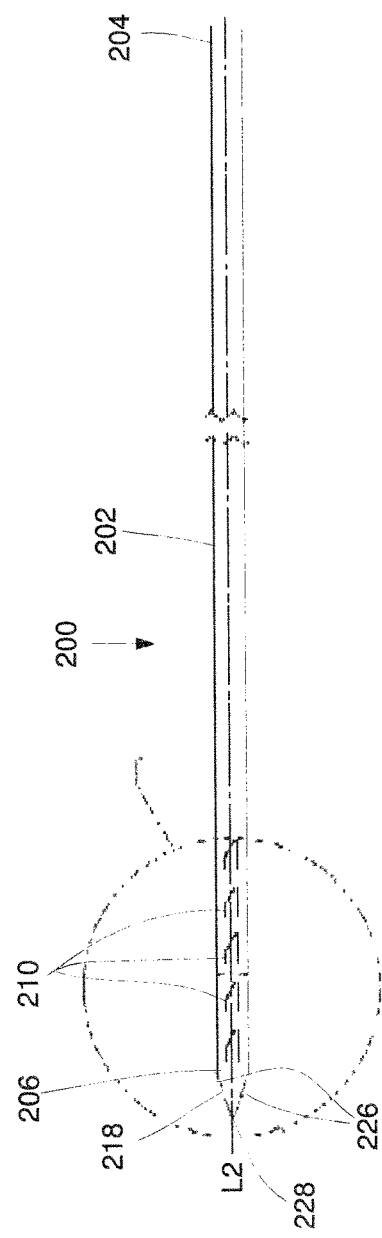
FIG. 8 shows a longitudinal side view of a device according to another exemplary embodiment of the present disclosure.

As shown in FIGS. 8-11, a device 200 according to another exemplary embodiment of the present disclosure is substantially similar to the device 100 described above except that, rather than vents formed via a pair of angled cuts extending laterally into the needle body as described above in regard to the device 100, the device 200 comprises a needle body 202 including vents formed via tabs 210 cut into a wall 220 of the needle body 202. As shown in FIG. 8, the needle body 202 is substantially similar to the needle body 102, extending along a longitudinal axis L2 from a proximal end 204 to a distal end 206 and including a channel 208 extending therethrough. The distal end 206 may include a tapered tip 218 defined via a pair of angled cuts 226 which meet at a point 228 within a plane extending through the longitudinal axis L2.

The device 200 may include a plurality of tabs 210 extending along a portion of a length of the needle body 202. Each tab 210 extends from a distal end 222 which remains connected to the wall 220 to a free, second end 224. The tabs 210 may be formed via cuts 214 extending into the wall 220 to define the tabs 210. Thus, as the device 200 is inserted distally into target tissue, a tissue sample may be collected within the channel 208, while liquids and gases are vented through the cuts 214 in the wall 220 defining the tabs 210. The tabs 210 may take any of a variety of shapes and sizes so long as the tabs 210 are prevented from catching onto tissue as the device 200 is being inserted distally through the target tissue. As shown in FIG. 11, a desired number of the tabs 210 may be crimped inward toward the longitudinal axis L2 to increase a holding strength of a tissue sample within the channel 208 and to increase an opening through the wall 220 formed via the tab 210. Where the tab(s) 210 are crimped inward, a proximal edge 230 defining the opening may cut tissue as the device 200 is being inserted into the target tissue, collecting additional tissue in the channel 208.

It will be apparent to those skilled in the art that variations can be made in the structure and methodology of the present disclosure, without departing from the scope of the disclosure. Thus, it is intended that the present disclosure cover the modifications and variations of this disclosure provided that they come within the scope of the appended claims and their equivalents.

What is claimed is:

1. A device for collecting a tissue sample, comprising:
a needle body extending along a longitudinal axis from a proximal end to a distal end and including a channel extending longitudinally therethrough; and
a plurality of cut outs extending laterally into the needle body, each of the cut outs defined by a first cut and a second cut, the first cut extending from an exterior surface of the needle body into the channel distally toward the longitudinal axis at a first angle relative to the longitudinal axis, the second cut extending from the exterior surface of the needle body into the channel distally toward the longitudinal axis at a second angle relative to the longitudinal axis so that the first cut and the second cut meet to form an acute angle.

2. The device of claim 1, wherein a first set of the plurality of cut outs extends along a length of a first side of the needle body.

3. The device of claim 2, wherein a second set of the plurality of cut outs extends along a length of a second side of the needle body substantially opposing the first side.

4. The device of claim 1, wherein a portion of a wall between adjacent cut outs is crimped inward toward a longitudinal axis of the needle body so that the portion of the wall extends into the channel.

5. The device of claim 1, wherein adjacent cut outs of the plurality of cut outs are equally spaced from one another along a length of the needle.

6. The device of claim 1, wherein the first cut and the second cut of each of the plurality of cut outs extend at an angle relative to the longitudinal axis ranging from between 20 and 60 degrees.

7. The device of claim 1, wherein an angle between the first and second cuts of each of the plurality of cuts outs ranges between 3 and 15 degrees.

8. The device of claim 1, wherein edges of the plurality of cut outs are sharpened to cut tissue as the device is being withdrawn from a target tissue.

9. The device of claim 1, wherein the distal end of the needle body includes a tapered distal tip.

* * * * *